United States Patent [19]

Lekholm

[11] Patent Number: 4,817,606

[45] Date of Patent: Apr. 4, 1989

[54] BODY ACTIVITY CONTROLLED HEART PACER

[75] Inventor: Anders Lekholm, Bromma, Sweden

[73] Assignee: Siemens Aktiengesellschaft, Berlin and Munich, Fed. Rep. of Germany

[21] Appl. No.: 124,552

[22] Filed: Nov. 24, 1987

[51] Int. Cl.$^4$ .................... A61B 1/00; H05G 00/00
[52] U.S. Cl. .................................................. 128/419 PG
[58] Field of Search ...................... 128/419 P, 419 PG

[56] References Cited

U.S. PATENT DOCUMENTS

| 4,428,378 | 1/1984 | Anderson et al. | 128/419 PG |
| 4,516,579 | 5/1985 | Irnich | 128/419 PG |

FOREIGN PATENT DOCUMENTS 0089014 9/1983 European Pat. Off. ...... 128/419 PG

OTHER PUBLICATIONS

Sensolog 703 Physician's Manual.
"Characteristics and Clinical Effects of Myopotential Signals in a Unipolar DDD Pacemaker Population", Pace, vol. 9, Nov.-Dec. 1986, pp. 1019-1024.
"New Developments for Upper Rate Response in DDD Pacing", Pace, vol. 9, Nov.-Dec. 1986, pp. 1047-1049.

Primary Examiner—Francis Jaworski
Assistant Examiner—George Manuel
Attorney, Agent, or Firm—Hill, Van Santen, Steadman & Simpson

[57] ABSTRACT

A body activity sensor in a rate adaptive pacer responds to myoelectrical signals in the patient's electrocardiogram (ECG). These myoelectrical signals are a measure of body activity and thus control the pulse generation rate of the pacer. Preferably, the myoelectrical signals are obtained by filtering out high frequency portions from the ECG and processing these filtered frequency portions.

12 Claims, 1 Drawing Sheet

BODY ACTIVITY CONTROLLED HEART PACER

BACKGROUND OF THE INVENTION

1. Field of the Invention

The present invention relates to a body activity controlled heart pacer for pacing the heart of a patient.

2. Description of the Prior Art

Such a pacer, which utilizes a body impedance measurement for obtaining a respiratory signal as the body activity signal that controls the stimulation rate is, for example, described in European Patent Application No. 0 089 014 (Plicchi et al.). A further pacer of this kind, which implements a piezoelectric motion sensor for delivering the body activity signal is known through U.S. Pat. No. 4,428,378 (Anderson et al.). Yet another such pacer, which also employs a piezoelectric motion sensor but processes the sensed signals in a manner different from Anderson et al, is marketed by Siemens-Elema as SENSOLOG 703 (see, for example, Siemens brochure A 91003-M 3372-L 943-01-7600).

Myopotentials are a further body activity signal, which have thus far been considered to be undesirable noise signals, since they can hinder—especially in the case of unipolar pacemakers—the correct detection of the QRS complex in the electrocardiogram. In the past, extremely sophisticated detectors were required, to discriminate between the QRS complexes and the myoelectrical signal components, which can sometimes reach amplitudes approaching 50 percent of the maximum QRS deflection.

SUMMARY OF THE INVENTION

It is an object of the present invention to provide a body activity controlled heart pacer which monitors a body activity previously not utilized for supplying a body-activity signal. It is a further object of the present invention to provide a pacer, which monitors a body activity in an especially simple manner, without using additional sensors.

According to the present invention, a body activity controlled heart pacer for pacing the heart of a patient is provided, which comprises:
(a) pulse generating means for generating stimulation pulses at a basic rate;
(b) means for sensing body activity and for generating a body activity signal;
(c) controlling means for controlling said pulse generating means such that said basic rate is varied as a function of said body activity signal,
wherein said means for sensing body activity includes a means for sensing myoelectrical signals, and wherein said controlling means control said pulse generating means such that said basic rate is varied as a function of said myoelectrical signals.

Instead of attempting to surpress the myopotentials, the heart pacer utilizes these "noise signals" to control the frequency of the pulse generator. Also, using myopotentials to regulate the pulse generation frequency allows for a reduction in the sensitivity setting of the pacer's QRS detector, because it is no longer imperative to detect each and every QRS complex. In the event that the detector misses a QRS complex, the stimulation pulse supplied by the generator will not be detrimental, since it will in any case be generated at a frequency conforming to the activity level of the patient.

The foregoing and other objects, features and advantages of the invention will be apparent from the following more particular description of a preferred embodiment of the invention, as illustrated in the accompanying drawings.

DESCRIPTION OF THE PREFERRED EMBODIMENT

Figure 1:
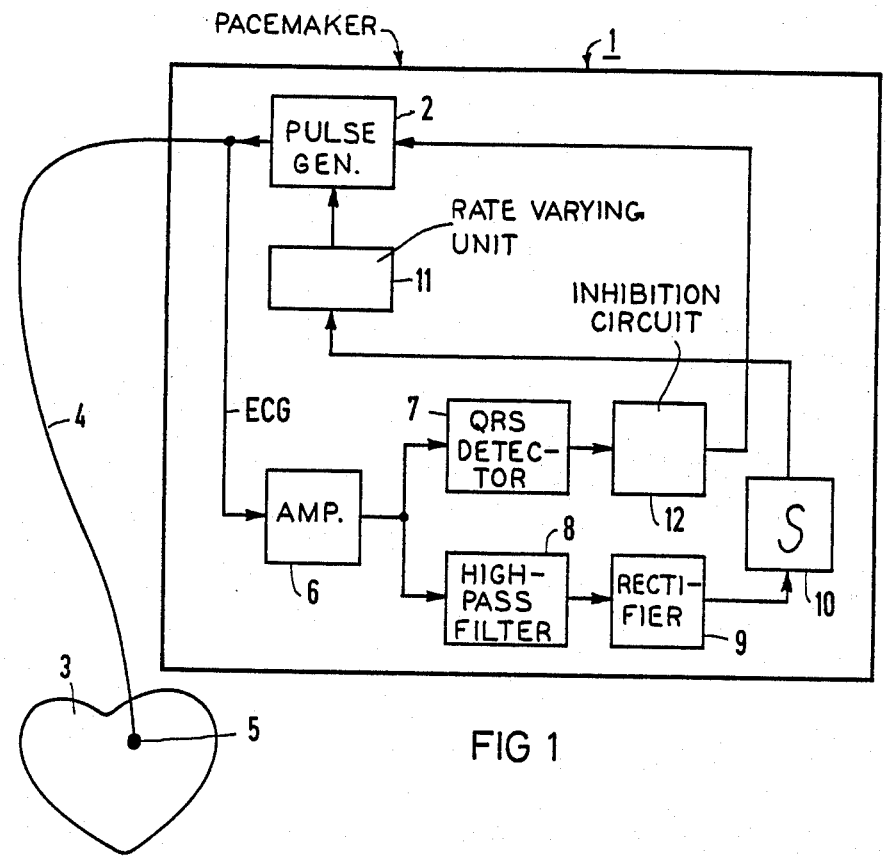
FIG. 1 is a schematic block diagram of a heart pacer controlled by a myoelectrical signal according to the principles of the present invention.

In FIG. 1 a heart pacer 1 is shown which includes a stimulation pulse generator 2, which generates stimulation pulses at a basic rate. These stimulation pulses are transmitted to a patient's heart 3 through pacing lead 4 to a stimulation electrode 5 inserted in the heart 3.

The stimulation electrode 5 together with the pacemaker housing (functioning as the return electrode, not shown) also serves as a device for sensing the electrocardiogram (ECG) of the heart. The ECG is passed through amplifier 6 to both a QRS detector 7 and a high pass filter 8. The high pass filter 8 filters out signal portions of the ECG, the frequencies of which are higher than the highest frequencies characteristic of the ECG. The filtered portions are rectified by a rectifier 9 and the rectified portions are integrated by integrator 10 to form an average signal. The average signal is delivered to the input of a stimulation rate varying unit 11. This stimulation rate varying unit 11 alters the basic rate of the stimulation pulse generator 2 as a function of the average signal of integrator 10, which signal is a measure of body activity.

Such a system could also be realized by using a comparator stage to pass only those high frequency signal components with amplitudes higher than a given preset threshold. After establishing the duration of these high amplitude signal portions, the stimulation rate varying unit 11 can use the resulting values to control the pulse generation frequency accordingly. A more advanced version of the system may include a QRS-detector containing a pattern-recognition circuit that identifies each QRS-complex. Such a circuit is described in U.S. Pat. No. 4,516,579, the teachings of which are is hereby incorporated by reference.

The QRS detector 7 detects the occurrence of a QRS complex. Its output signal is supplied to an inhibition unit 12, the output signal of which controls the stimulation pulse generator 2 in the inhibition mode.

Figure 2:
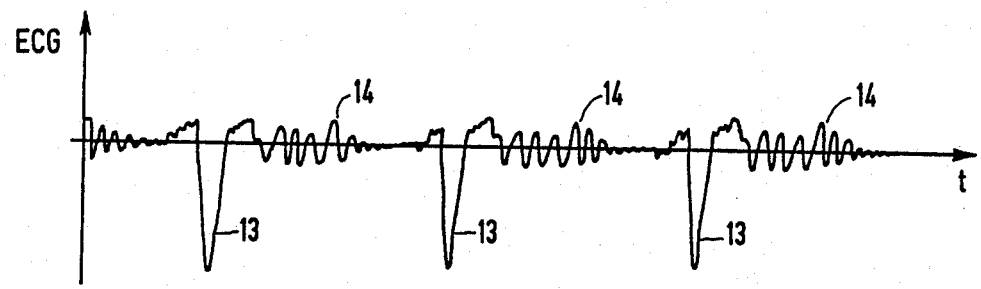
FIG. 2 is an electrocardiogram containing myoelectrical signals.

In FIG. 2 the QRS complexes in the ECG are generally designated with the reference numeral 13. The high frequency portions therebetween define the myoelectrical signals and are referenced by 14.

The myopotentials 14 are influenced by various body activities, including arm movement and respiration. Some or all of these body activities reflected in the myoelectrical signals can be utilized to control the frequency of the stimulation pulse generator 2. For example, the ECG signal can be processed such that only those portions of the myoelectrical signal reflecting primarily the patient's respiration rate control the pulse generation frequency of the heart pacer 1.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims appended hereto.

What is claimed is:

1. A body activity-controlled device for pacing the heart of a patient, comprising:
   pulse generating means for generating heart stimulation pulses at a basic rate;
   means for sensing body activity which includes means for sensing myoelectrical signals from said patient;
   means connected to said means for sensing body activity for identifying said myoelectrical signals and generating a body activity signal based thereon; and
   control means for controlling said pulse generating means to vary said basic rate as a function of said body activity signal.

2. A device as claimed in claim 1, wherein said means for identifying said myoelectrical signals comprises:
   means for rectifying said myoelectrical signals; and
   means for forming an average signal from the rectified myoelectrical signals,
and wherein said controlling means is a means for varying said basic rate as a function of said average signal.

3. A device as claimed in claim 2, wherein said means for forming an average signal is an integrator.

4. A device as claimed in claim 2, wherein said means for sensing body activity is a means for sensing electrocardiographic signals of the patient's heart, said electrocardiographic signals having highest frequencies, and said electrocardiographic signals also including said myoelectrical signals, and wherein said means for identifying said myoelectrical signals includes filter means for filtering signal portions from said electrocardiographic signals having frequencies which are higher than said highest frequencies, the signal portions filtered from said electrocardiographic signals being said myoelectric signals.

5. A device as claimed in claim 4, further comprising:
   a QRS detector to which said electrocardiographic signals is supplied; and
   means for controlling operation of said pulse generating means based on the output of said QRS detector.

6. A body activity-controlled device for pacing the heart of a patient, comprising:
   pulse generating means for generating heart stimulation pulses at a basic rate;
   means for sensing electrocardiographic signals of the patient's heart, said electrocardiographic signals including myoelectrical signals, said myoelectrical signals changing with changing body activity;
   means for separating said myoelectrical signals from said electrocardiographic signals; and
   control means for controlling said pulse generating means to vary said basic rate as a function of said myoelectrical signals.

7. A device as claimed in claim 6, wherein said means for separating said myoelectrical signals is a high pass filter, and wherein said myoelectrical signals are passed by said high pass filter.

8. A device as claimed in claim 7, further comprising:
   means for rectifying said myoelectrical signals passed by said high pass filter; and
   means for integrating the rectified myoelectrical signals.

9. A device as claimed in claim 6, further comprising:
   a QRS detector to which said electrocardiographic signals from said means for sensing electrocardiographic signals is supplied; and
   means for controlling operation of said pulse generator based on the output of said QRS detector.

10. A method for operating a pacemaker for pacing the heart of a patient comprising the steps of:
    generating heart stimulation pulses at a basic pacing rate;
    sensing electrocardiographic signals of the patient's heart which includes myoelectrical signals;
    separating the myoelectrical signals from the electrocardiographic signals; and
    varying the basic pacing rate of the heart stimulation pulses as a function of said myoelectrical signal.

11. A method as claimed in claim 10, wherein the step of separating said myoelectrical signals is further defined by high pass filtering said electrocardiographic signals with the myoelectrical signals being passed by said high pass filtering.

12. A method as claimed in claim 10, comprising the additional steps of:
    rectifying the myoelectrical signals after said high pass filtering thereof; and
    integrating the rectified myoelectrical signals with respect to time.

* * * * *